United States Patent [19]

Friese et al.

[11] Patent Number: 5,795,454
[45] Date of Patent: Aug. 18, 1998

[54] SEAL FOR A SENSOR ELEMENT OF A GAS SENSOR

[75] Inventors: Karl-Hermann Friese, Leonberg; Helmut Weyl, Schwieberdingen; Romuald Fries, Weissach; Hans-Martin Wiedenmann, Stuttgart; Anton Hans, Ludwigsburg, all of Germany

[73] Assignee: Robert Bosch GmbH, Stuttgart, Germany

[21] Appl. No.: 569,074

[22] PCT Filed: May 11, 1994

[86] PCT No.: PCT/DE94/00537

§ 371 Date: Dec. 4, 1995

§ 102(e) Date: Dec. 4, 1995

[87] PCT Pub. No.: WO94/29710

PCT Pub. Date: Dec. 22, 1994

[30] Foreign Application Priority Data

Jun. 5, 1993 [DE] Germany .................. 43 18 789.7

[51] Int. Cl.$^6$ .................... G01N 27/407; F16J 15/14
[52] U.S. Cl. .................... 204/424; 204/426; 204/427; 204/428; 277/316; 277/650; 277/936; 277/938; 277/939; 277/941; 277/943
[58] Field of Search .................... 204/421–429; 277/316, 650, 936, 938, 939, 941, 943

[56] References Cited

U.S. PATENT DOCUMENTS 3,891,529  6/1975  Beesch .................... 204/428
3,960,692  6/1976  Weyl et al. .................... 204/428
4,088,555  5/1978  Kita .................... 204/428
4,141,813  2/1979  Kita et al. .................... 204/428
4,732,663  3/1988  Kato et al. .................... 204/426
4,818,363  4/1989  Bayha et al. .
4,986,892  1/1991  Kato et al. .................... 204/427
5,246,562  9/1993  Weyl et al. .

FOREIGN PATENT DOCUMENTS 0087626  9/1983  European Pat. Off. .
2350253  4/1975  Germany .
2645573  4/1977  Germany .
 265489  6/1977  Germany .

*Primary Examiner*—T. Tung
*Attorney, Agent, or Firm*—Spencer & Frank

[57] ABSTRACT

A seal for a sensor element of a gas sensor for determining the oxygen content in gases including exhaust gases of an internal combustion engine, which seal seals the sensor element in a longitudinal bore of a housing, the seal including a sealing stack which is positioned within the longitudinal bore of the housing and around the sensor element in use and which is comprised of two sealing bodies and an additional seal positioned between the two sealing bodies. The two sealing bodies are comprised of a pre-sintered ceramic material. The additional seal is comprised of a pre-pressed powder material and has a porosity which is lower than that of the two sealing bodies. The two sealing bodies and the additional seal are compressed together within the longitudinal bore in use, whereby at least the additional seal is deformed so that the sensor element is sealed in a gap-free manner within the longitudinal bore. The pre-pressed powder material of the additional seal may consist essentially of a ductile metal, which may be one of nickel or copper, or graphite which may be fiber-reinforced.

14 Claims, 1 Drawing Sheet

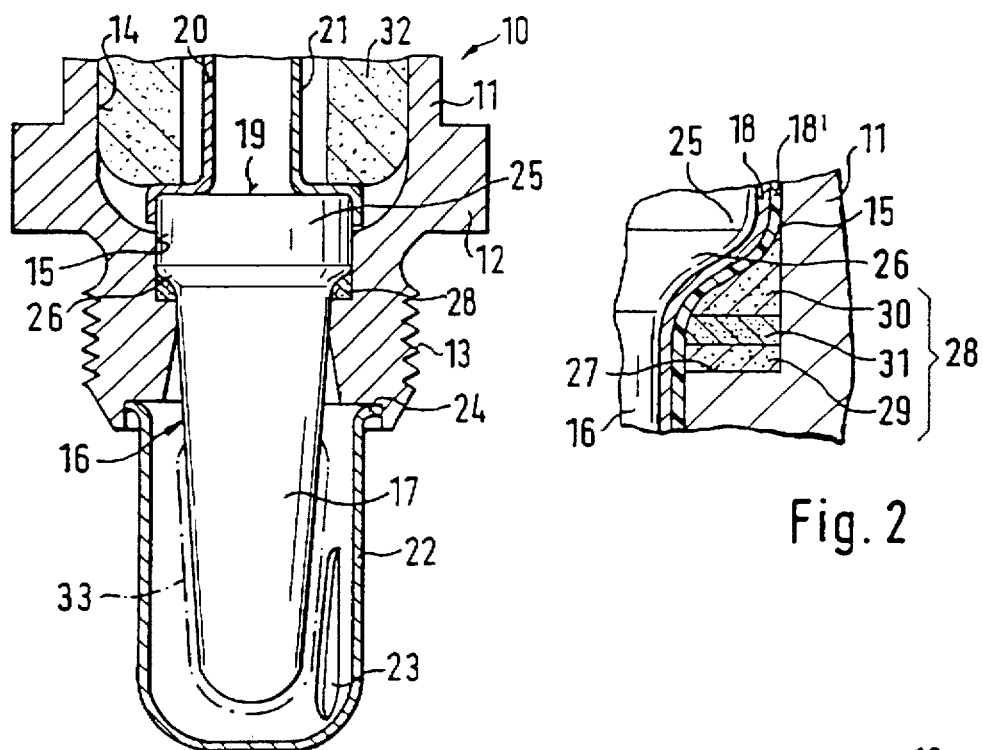
Fig. 1
Fig. 2
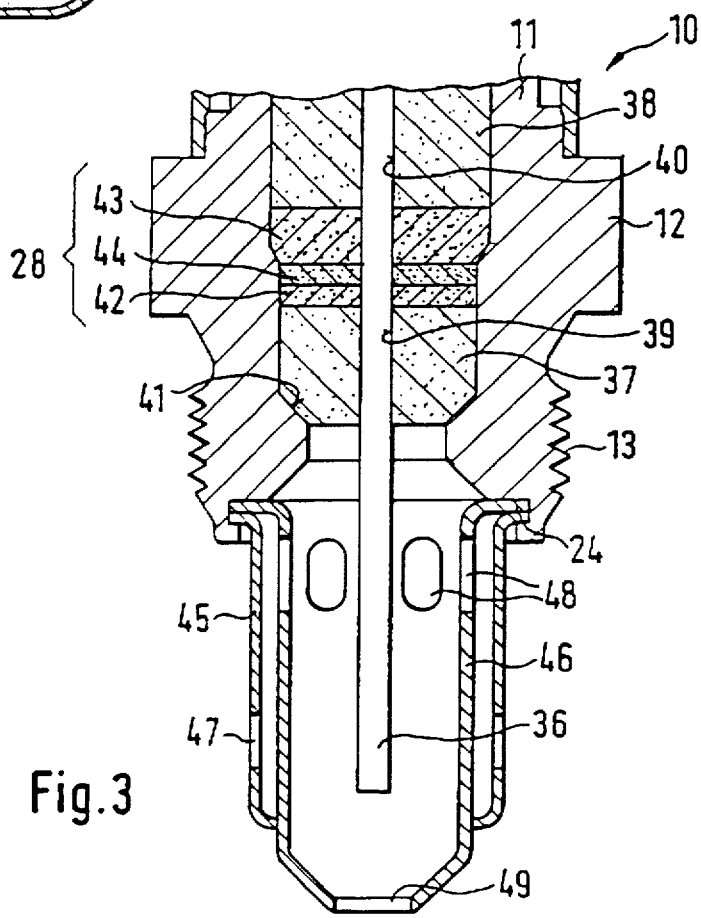
Fig. 3

SEAL FOR A SENSOR ELEMENT OF A GAS SENSOR

BACKGROUND OF THE INVENTION

1. Field of the Invention

The invention is based on a seal for a sensor element of a gas sensor particularly for determining the oxygen content in exhaust gases of internal combustion engines, which seal seals the sensor element in a longitudinal bore of a housing. The sensor elements used to determine the oxygen content in exhaust gases of internal combustion engines include, on the one hand, a so-called finger construction, in which an electrochemical solid electrolyte is configured as a tube that is closed on one side and is fixed in the housing in a sealed manner. In the other known, so-called wafer sensors, a planar, oxygen-conductive solid electrolyte is likewise sealingly fixed in the housing.

2. Description of the Related Art.

In DE-OS 41 26 378, a seal for a wafer sensor is described which is located between two ceramic formed parts disposed in the housing, with the ceramic formed parts securing the sensor element in the housing. The seal in this instance is made of soapstone.

Finger sensors are divided into potential-free and potential-bound gas sensors. In potential-bound finger sensors, the conductor path of the outer electrode is contacted with the housing by means of an electrically-conductive sealing ring. In potential-free finger sensors, each electrode connector is guided directly to a control device, so that no electrical contact with the housing is permitted. For potential-free finger sensors, it has already been proposed to use a deformable, electrically-insulating, ceramic sealing ring.

Both the deformable ceramic sealing ring in the finger sensor and the seal material used in the wafer sensor are pre-sintered at low sintering temperatures, by means of which a residual porosity is retained, even under high pressing forces, which has the disadvantage that water and fuel diffuse through the seal due to capillary forces.

SUMMARY OF THE INVENTION

In contrast, the seal of the invention has a deformable additional seal which has a lesser porosity than two sealing bodies, is disposed between the two sealing bodies, and has the advantage that it is impermeable to liquids, particularly fuel. A seal with respect to liquid fuel is required particularly if fuel enters the exhaust pipe when the internal combustion engine experiences difficulty starting.

Advantageous modifications and improvements of the seal disclosed in the main claim are possible with the measures outlined in the dependent claims. Thus, the sealing bodies may be pre-sintered and may be pressed, with the additional seal, into the longitudinal bore, wherein the additional seal becomes deformed during pressing such that the sensor element is disposed gap-free in the longitudinal bore. The additional seal may be a pre-formed sealing disk or a pre-formed sealing ring. The additional seal may be made of a ductile metal, preferably nickel or copper. The ductile metal can be used in the form of a pre-pressed powder or in solid form. The additional seal may be made of graphite and the graphite may be fiber-reinforced. A particularly good seal is achieved when the sealing body and the additional seal are pressed together in the housing. This causes the additional seal to lie gap-free between the sensor element and the housing. Graphite has proven to be especially well-suited as a material for the additional seal: because of its lamellar structure, it is impermeable to water and fuel under correspondingly high compression.

BRIEF DESCRIPTION OF THE DRAWINGS

Two embodiments of the invention are illustrated in the drawing and described in detail in the following description.

FIG. 1 shows a longitudinal section through the exhaust-gas-side part of a gas sensor having a finger sensor, FIG. 2 shows an enlarged section of the seal according to FIG. 1, and FIG. 3 shows a longitudinal section through the exhaust-gas-side part of a gas sensor having a wafer sensor.

DESCRIPTION OF THE PREFERRED EMBODIMENTS

FIG. 1 shows an electrochemical oxygen gas sensor 10 having a metallic housing 11 which has a hexagonal nut 12 and a thread 13 as fastening means for installation into a measuring gas pipe, not shown. The housing 11 has a longitudinal bore 14 having a receptacle 15 for a finger sensor 16 serving as a sensor element. The receptacle 15 has an annular bottom surface 27.

The finger sensor 16 is an electrochemical oxygen sensor which is known per se and is preferably used for measuring the oxygen partial pressure in exhaust gases. The finger sensor 16 has a tubular solid electrolyte body 17 whose end section on the side of the measured gas is closed. A measuring electrode, not shown, is disposed, with a protective layer 33 above it, on the exterior side exposed to the measured gas, and a reference electrode, likewise not shown, which is exposed to a reference gas, for example air, is disposed on the side facing the interior. The finger sensor 16 has on the side of its connector a bead-like head 25 having a formed-on shoulder 26 and an annular front face 19. On the side of the measured gas, the finger sensor 16 is surrounded, with spacing, by a protective pipe 22, which has openings 23 for the entrance or exit of the measured gas.

The protective pipe 22 is secured, by means of a flange 24, to the end of the housing 11 on the side of the measured gas.

The measuring electrode and the reference electrode are respectively guided to the connection-side annular surface 19 of the finger sensor 16 by means of electrode conductor paths, of which the conductor path 18 of the measuring electrode is shown in FIG. 2. The conductor path 18 is provided in order to prevent ground contact with the housing 11 with an insulating cover layer 18'. A reference electrode contact part 20 and a measuring electrode contact part 21 are seated on the annular surface 19. The two contact parts 20, 21 are connected to electrical connections which are not shown.

The receptacle 15 formed in the longitudinal bore 14 is structured in such a way that the bead-like head 25 of the finger sensor 16 is guided radially, and forms a seal zone between the shoulder 26 of the finger sensor 16 and the bottom surface 27 in which a sealing stack 28 is disposed. According to FIG. 2, the sealing stack 28 has a sealing ring 29 on the side of the measured gas, a sealing ring 30 on the side of the connections, and an additional sealing ring 31 disposed between them. The two sealing rings 29, 30 are made of a material which has been porously sintered at low sintering temperatures, so that they are deformable under a pressing force. An example of a material suited for this is magnesium aluminum silicate (steatite). The additional sealing ring 31, in contrast, is made of graphite, which is likewise deformable under the effect of the pressing force.

The pre-sintered sealing ring 29 on the side of the measured gas, the additional sealing ring 31 and the pre-sintered sealing ring 30 on the side of the connections are inserted into the receptacle 15 in order to produce the sealing stack 28. The finger sensor 16 is placed, with its shoulder 26, onto the connection-side sealing ring 30. Due to the effect of a pressing force on the finger sensor 16, the two sealing rings 29, 30 are deformed in such a way that they are adapted to the shoulder 26 and the receptacle 15. At the same time, the additional sealing ring 31 is compromised in such manner that a sufficient radial pressing force arises between the housing 11 and the finger sensor 16 to hold the finger sensor 16 gap-free in the longitudinal bore 14. The radial pressing force has a uniform effect on the insulating cover layer 18' so that this layer is not damaged.

Once the finger sensor 16 has been pressed into the receptacle 15, it is held by the insulating sleeve 32 engaging the contact parts 20, 21. The oxidation of the graphite which sets in as of approximately 600° C. under atmospheric conditions is extensively prevented by the embedding of the additional sealing ring 31 between two virtually air-impermeable sealing rings 29, 30 made of ceramic. This is also the case for metallic additional seals made of nickel or copper in solid form or in The form of a pre-pressed powder.

A second embodiment of a measuring sensor 10 having a wafer sensor 36 is shown in FIG. 3. In this instance, the longitudinal bore 14 has a shoulder-shaped narrowing 41, on which a measured-gas-side ceramic formed part 37 lies. A connection-side ceramic formed part 38 is disposed in the longitudinal bore, at a distance from the ceramic formed part 37 on the side of the measured gas. The longitudinal bore 14 in this embodiment is stepped in such a way that the connection-side ceramic formed body 38 has a larger diameter than the ceramic formed body 37 on the side of the measured gas. The ceramic formed parts 37 and 38 are configured with a central passage 39 and 40, respectively. The passages 39, 40 serve to receive the wafer sensor 36.

The sealing stack 28 is located between the spaced ceramic formed parts 37, 38. Similarly to the first embodiment, the sealing stack 28 includes a sealing disk 42 on the side of the measured gas, and a sealing disk 43-on the side of the connections, between which disks an additional sealing disk 43 is disposed, for example, with the sealing disk 43 on the side of the connections being configured thicker than sealing disk 42 on the side of the measured gas. In addition, the transition of the longitudinal bore 14 from the larger diameter to the narrower diameter in the region of the connection-side sealing disk 43 is configured as a conical transition. As in the first embodiment, the two sealing disks 42 and 43 are made of, for example, a pre-sintered ceramic material. The additional sealing disk 44 is likewise made of graphite.

The wafer sensor 36 is sealed by means of the placement of the measured-gas-side sealing disk 42, the additional sealing disk 44, the connection-side sealing disk 43 and the connect-on-side ceramic formed body 38 on top of the measured-gas-side ceramic formed body 37. Due to the exertion of a pressing force, the sealing disks 42 and 43 and the additional sealing disk 44 are pressed together, becoming deformed in the process. As in the first embodiment, because of the deformation, a radial pressing force arises between the housing 11 and the wafer sensor 36, so that the wafer sensor 36 lies gap-free in the longitudinal bore. Also in this instance, the radial pressing force is selected to be uniform, so that it does not cause damage to the wafer sensor 36.

In the present second embodiment, the protective pipe 22 is configured to have two walls, with an outer protective pipe 45 and an inner protective pipe 46, to prevent condensation water from reaching the wafer sensor 36. External gas openings 47 are provided in the outer protective pipe 45; inner gas openings 48 are disposed, with axial offset from these openings, on the inner protective pipe 46. For more thorough rinsing, an additional opening.49 is cut into the bottom of the inner protective pipe 46.

To preclude damage to the sensor element while the sealing stack 28 is being pressed, ductile materials can be used for the additional seal 31 or 44 which have a hardness that must be less than that of the cover layer 18' of the finger sensor 16 or the ceramic used in the wafer sensor 36.

What is claimed is:

1. A seal for a sensor element of a gas sensor for determining the oxygen content in gases including exhaust gases of an internal combustion engine, which seal seals the sensor element in a longitudinal bore of a housing, the seal comprising:

a sealing stack which is positioned within the longitudinal bore of the housing and around the sensor element in use and which is comprised of two sealing bodies and an additional seal positioned between and directly adjoining the two sealing bodies, wherein the two sealing bodies are comprised of a pre-sintered ceramic material, wherein the additional seal is comprised of a pre-pressed powder material, wherein the two sealing bodies and the additional seal are compressed together within the longitudinal bore in use and are deformed into respective powders so that the sensor element is sealed in a gap-free manner within the longitudinal bore, and wherein following compressing and deformation, the additional seal has a porosity which is lower than that of the two sealing bodies.

2. The seal as defined in claim 1, wherein the pre-pressed powder material of the additional seal consists essentially of a ductile metal.

3. The seal as defined in claim 2, wherein the ductile metal is one of nickel or copper.

4. The seal as defined in claim 1, wherein the pre-pressed powder material of the additional seal comprises graphite.

5. The seal as defined in claim 4, wherein the graphite is fiber-reinforced.

6. The seal as defined in claim 4, wherein the pre-pressed powder material of the additional seal consists essentially of graphite.

7. The seal as defined in claim 1, wherein the pre-sintered ceramic material of the two sealing bodies consists essentially of magnesium aluminum silicate.

8. A seal for a sensor element of a gas sensor for determining the oxygen content in gases including exhaust gases of an internal combustion engine, which seal seals the sensor element in a longitudinal bore of a housing, the seal comprising:

a sealing stack which is positioned in use within the longitudinal bore of the housing and around the sensor element and which is comprised of two sealing bodies and an additional seal positioned between and directly adjoining the two sealing bodies, wherein the two sealing bodies have a form which is one of a ring and a disk and are comprised of a pre-sintered ceramic material which is porously sintered at a low sintering temperature so that it is deformable under a pressing force, wherein the additional seal has a form which is one of a ring and a disk and is comprised of a pre-pressed powder material, wherein the two sealing bodies and the additional seal are compressed together within the longitudinal bore in use and are deformed into respective powders so that the sensor element is sealed in a gap-free manner within the longitudinal bore, and wherein following compressing and deformation, the additional seal has a porosity which is lower than that of the two sealing bodies.

9. The seal as defined in claim 8, it wherein the pre-pressed powder material of the additional seal consists essentially of a ductile metal.

10. The seal as defined in claim 9, wherein the ductile metal is one of nickel or copper.

11. The seal as defined in claim 8, wherein the pre-pressed powder material of the additional seal comprises graphite.

12. The seal as defined in claim 11, wherein the graphite is fiber-reinforced.

13. The seal as defined in claim 11, wherein the pre-pressed powder material of the additional seal consists essentially of graphite.

14. The seal as defined in claim 8, wherein the pre-sintered ceramic material of the two sealing bodies consists essentially of magnesium aluminum silicate.

* * * * *